United States Patent [19]
Hoffmann et al.

[11] Patent Number: 5,538,736
[45] Date of Patent: Jul. 23, 1996

[54] ACTIVE SUBSTANCE-CONTAINING PLASTER FOR THE CONTROLLED ADMINISTRATION OF ACTIVE SUBSTANCES TO THE SKIN

[75] Inventors: Hans R. Hoffmann, Neuwied; Karin Wolter, Melsbach; Günter Simon, Hillesheim; Peter Barth, Neuwied, all of Germany

[73] Assignee: LTS Lohmann Therapie-Systeme GmbH, Andernach, Germany

[21] Appl. No.: 307,353

[22] Filed: Sep. 14, 1994

Related U.S. Application Data

[63] Continuation-in-part of Ser. No. 68,861, May 28, 1993, abandoned, which is a continuation of Ser. No. 642,714, Jan. 17, 1991, abandoned, which is a continuation of Ser. No. 276,316, Nov. 25, 1988, abandoned, filed as PCT/DE88/00180, Mar. 22, 1988.

[30] Foreign Application Priority Data

Apr. 28, 1987 [DE] Germany .......................... 37 14 140.6

[51] Int. Cl.⁶ .................................................. A61F 13/00
[52] U.S. Cl. ............................................ 424/448; 424/449
[58] Field of Search .................................... 424/448, 449

[56] References Cited

U.S. PATENT DOCUMENTS

| | | | |
|---|---|---|---|
| 4,297,995 | 11/1981 | Golub | 128/156 |
| 4,622,031 | 11/1986 | Sibalis | 604/20 |
| 4,666,441 | 5/1987 | Andriola | 604/897 |
| 4,917,688 | 4/1990 | Nelson | 604/306 |

*Primary Examiner*—D. Gabrielle Phelan
*Attorney, Agent, or Firm*—Kalish & Gilster

[57] ABSTRACT

The invention relates to an active substance-containing plaster for the controlled administration of active substances to the skin, which has a back and a skin side, with a back layer, an active substance reservoir divided substantially perpendicularly to the skin contact surface of the plaster and having one or more active substances, a contact adhesive device on the skin side and optionally a cover layer detachable prior to the application of the plaster, whereas at least one active substance reservoir part (12) is detachable from the skin, while leaving behind one or more active substance reservoir parts (13) on the skin. For this object there is provided that the part of the active substance reservoir remaining on the skin is having a better adhesion to the skin than to the back layer (11).

30 Claims, 3 Drawing Sheets

ACTIVE SUBSTANCE-CONTAINING PLASTER FOR THE CONTROLLED ADMINISTRATION OF ACTIVE SUBSTANCES TO THE SKIN

CROSS REFERENCE TO PRIOR APPLICATIONS

This application is a continuation-in-part of Ser. No. 08/068,861 filed May 28, 1993 now abandoned, which is a continuation of Ser. No. 07/642,714 filed Jan 17, 1991 now abandoned, which is a continuation of Ser. No. 07/276,316 filed Nov. 25, 1988 now abandoned which was filed as PCT/DE88/00180 on Mar. 22, 1988.

BACKGROUND AND SUMMARY OF THE INVENTION

The invention relates to an active substance-containing plaster for the controlled administration of active substances to the skin, which has a back and a skin side, with a back layer, an active substance reservoir subdivided substantially perpendicularly to the skin contact surface of the plaster and having one or more active substances, an adhesive device on the skin side and optionally a cover layer detachable prior to the application of the plaster, it being possible to reduce the size of the active substance release surface of the plaster by a predetermined amount by removing part of the active substance reservoir, as well as the use thereof and a process for the controlled administration of active substances to the skin.

The invention more particularly relates to those plasters used as transdermal therapeutic systems for the controlled administration of medical active substances or also cosmetically active substances to the human or animal skin. A therapeutic system is a medicament or active substance-containing means or administration form, which delivers one or more active substances in a continuous manner, at a predetermined rate and over a given time interval to a predetermined application point. These systems are therapeutic precision instruments, whose construction requires extraordinary measures in order to ensure continuous active substance release.

Plaster-like therapeutic systems have already been developed for the most varied uses and, apart from a topical effect, a systemic effect can also be obtained. The multiplicity of active substances applicable in this way and their different chemical, physical and pharmacological characteristics make it impossible to cover all therapeutic problems with a single system.

Numerous therapeutic systems for the administration of medical active substances to the skin are known, a summary being e.g. provided in Klaus Heilmann "Therapeutische Systeme" Ferdinand Enke Verlag, Stuttgart, 1977. The prior art systems were not able to provide a completely satisfactory action in all cases.

In the conventional structure of a transdermal plaster-like therapeutic system there is an active substance reservoir, which contains the active substance in solid, liquid or dissolved form and a pressure-sensitive adhesion layer (contact adhesive), through which the system is closely liked with the skin. It is important that a whole-area contact is ensured between the active substance release surfaces to the skin throughout the application of the systems, in order to make sure of the active substance release kinetics. This can be achieved not only through an uninterrupted adhesion layer, but also by restricted adhesion areas in the skin contact layer of the plaster.

Although the hitherto known plaster-like therapeutic systems permit a uniform or continuously decreasing application of an active substance over a predetermined time, they do not permit specific active substance release kinetics, such as a planned reduction of the active substance release after a predetermined time, or a graduated active substance release quantity per unit of time.

This measure is e.g. necessary if the active substance dose has to be reduced in a planned manner during the application period for therapeutic reasons. The same problem arises if, during the application of a combination product, the release of one active substance in the combination must be terminated after a predetermined time. In such cases, it is in principle possible to solve the problem by using two transdermal plasters, whereof one is removed at the given time. However, this leads to problems for patients, particularly if they are aged. Therefore it is easy to forget to apply the second plaster. In a combination of two plasters with different active substance release surfaces, there is also a risk of choosing the incorrect combination (two identical plasters), or the removal of the wrong plaster. The same complications occur if plasters with different active substances have to be combined and there is in this case also the problem of double storage. Thus, the use of two plasters leads to numerous disadvantages and the avoidance thereof forms an objective of the invention.

The proposal of combining two plasters, whereby part thereof can be detached with the aid of a predetermined breaking line, admittedly improves compliance, but leads to handling problems. Thus, the part to be detached can only be handled by raising from the skin and in undesired manner at least a part of the plaster still remaining on the skin is raised and must be firmly held during detachment. Thus, pressure is exerted on the sensitive transdermal system, which can negatively influence the active substance release rate.

U.S. Pat. No. 4,297,995 describes a manipulatable active substance plaster, in which the active substance reservoir is subdivided, but is integrated into a single plaster. The active substance reservoir parts are arranged in concentric rings about a disk-like central portion. The overall construction of the plaster with a mechanical fixing of the reservoir to the back layer only makes it possible to change the active substance release surface prior to the application of the plaster, i.e. prior to plaster application the doctor/patient can choose which dose is to be administered, but for changing the active substance release during plaster application, the plaster must be detached from the skin, while interrupting therapy and this can also lead to damage and contamination to the plaster support surface. As yet no satisfactory solution has been found for the associated problems of repositioning and the permanent refixing of the system to the skin.

Therefore the problem of the present invention is to provide an improved therapeutic transdermal system, which makes it possible to realize more complicated changes to the active substance release than have hitherto been possible.

This problem is solved by a plaster of the aforementioned type, which is characterized in that at least part of the active substance reservoir can be detached, while leaving one or more parts of said reservoir on the skin and the part of the active substance reservoir left behind on the skin has a better adhesion to the skin than to the back layer.

The present invention provides a transdermal drug delivery system that allows the user to easily and effectively remove part of the system, while leaving the remaining part intact and undisturbed. Such is of extreme utility in stepwise administration of drugs, such as nicotine, as well as other drugs, where the dosage must be changed as "plasters" are successfully applied over time. The system has at least two drug reservoirs, a first and second reservoir. The second reservoir is removed and the first remains attached to the akin. This is accomplished by the use of a peel-off layer which covers the back of the first reservoir, which is made of an essentially non-sticky material. A back layer, which covers and encloses the entire patch rests on top of the peel-off layer and the peel-off layer adheres to the first reservoir. When the back layer is removed, the second reservoir is lifted off the skin, but since the peel-off layer does not adhere to the back layer, the first reservoir remains and adheres to the skin. This allows the user to remove the desired reservoir with one hand and in-one motion.

Due to the fact that, according to the invention, the active substance reservoir is partly detachable whereby the part of the active substance reservoir which is not to be detached has a greater adhesion to the skin than to the back layer, after removing a predetermined plaster part with the active substance reservoir part adhering thereto, there is left behind a predetermined active substance reservoir part on the skin, which can e.g. be alone removed following the desired application period. Advantageously the active substance reservoir of the inventive plaster is in two parts.

In the case of given therapies with varying or marked concentration-fluctuating active substance administrations, it can also be advantageous for the active substance reservoir to be in three parts. The active substance release surfaces of the active substance reservoir parts can be geometrically identical or different. The active substance release surfaces can be juxtaposed, or one active substance reservoir part can completely surround one or more other active substance reservoir parts, considered in a flat or surface-based manner. The subdivision of the partial surfaces is dependent on the therapeutic requirements. Thus, e.g. one active substance reservoir part can circularly surround one or more other active substance reservoir parts.

The release surface—size ratio of one active substance reservoir part to another is preferably in the range between approximately 1:1 and 1:10. The same active substance or the same active substance combination can be present in all the active substance reservoir parts.

Particularly preferred products are plasters with the following active substances, but it is also possible to process random other transdermally administrable active substance combinations known to the medical Expert: asthma/bronchodilators, such as e.g. clenbuterol, proctaterol and salbutamol and vasodilators, such as e.g. bencyclane and cinnarizine, compounds to cause people to stop smoking, e.g., nicotine and lobeline.

Thus, with the aid of the inventive plaster, in such cases it is possible to reduce the administration dose in a planned and controlled manner during application.

However, the active substance reservoir parts can also contain different active substances or different active substance combinations, so that during application it is possible to interrupt or stop one active substance or active substance combination. Examples for different active substances in the active substance reservoir parts are: oestrogen/gestagen (contraceptives), dexamethasone/prednisolone (in the case of inflammatory, rheumatic muscle and joint diseases), nitroglycerin/β-blockers (for cardiac diseases), phenytoin/phenobarbital/caffeine (for epilepsy) and amitriptyline/chlordiazepoxide (psychopharmaceuticals).

All suitable active substances belong to the groups having either a topical or systemic action. In at least one active substance reservoir part there can be different active substance/active substance combinations as compared with the other active substance reservoir part or parts.

The preferred use of the inventive plasters is in local and systemic, transdermal active substance administration in human or animal medicine or in cosmetics.

BRIEF DESCRIPTION OF THE DRAWINGS

The invention is described in greater detail hereinafter relative to non-limitative embodiments and with reference to the attached drawings, which are not true to scale and wherein show.

DESCRIPTION OF PREFERRED
EMBODIMENTS OF THE INVENTION

The preferred embodiments of the invention shown in the individual drawings will now be described. The active substance reservoir part left last on the skin is referred to as the first active substance reservoir part, while the second and third active substance reservoir parts are those which are detached with the back layer.

Figure 1:
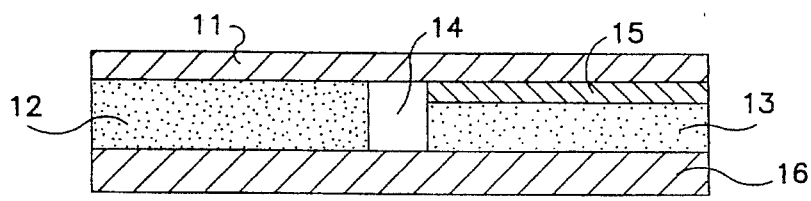
FIG. 1 a cross-section through a first embodiment of an inventive plaster with a two-part active substance reservoir.

FIG. 1 shows a preferred embodiment of an inventive, optionally circular or angular plaster with a two-part, adhesive active substance reservoir in cross-section. The second active substance reservoir part 12 directly adheres to the back layer 11 and is separated from the first adhesive active substance reservoir part 13 by a reservoir separating layer 14, which can be constructed as a gap or space between the active substance reservoir parts, or can be filled by an inert separating material. Active substance reservoir part 13 adheres to the back layer 11 by means of a peel-off layer 15, which brings about a gradual adhesion of the two active substance reservoir parts 12,13 to the back layer. The peel-off layer 15 can e.g. by a polymer or metal film or foil, a textile fabric or a laminate thereof and following the removal of the back layer 11 with the second active substance reservoir part 12 forms a protective layer for the first active substance reservoir part 13 left on the skin in order to protect the latter. The adhesion of the first active substance reservoir part 13 to the skin must be greater than the adhesion between the peel-off layer 15 and the back layer 11. The protective layer 16 is removed prior to the application of the plaster. By the use of the same dotting system for the surfaces representing the active substance reservoir parts 12,13 in FIG. 1, it is made clear that in both active substance reservoir parts 12,13 there is the same active substance or active substance combination, so that with the plaster according to FIG. 1 it is possible to bring about a gradual decrease of the active substance release to the skin.

Figure 2:
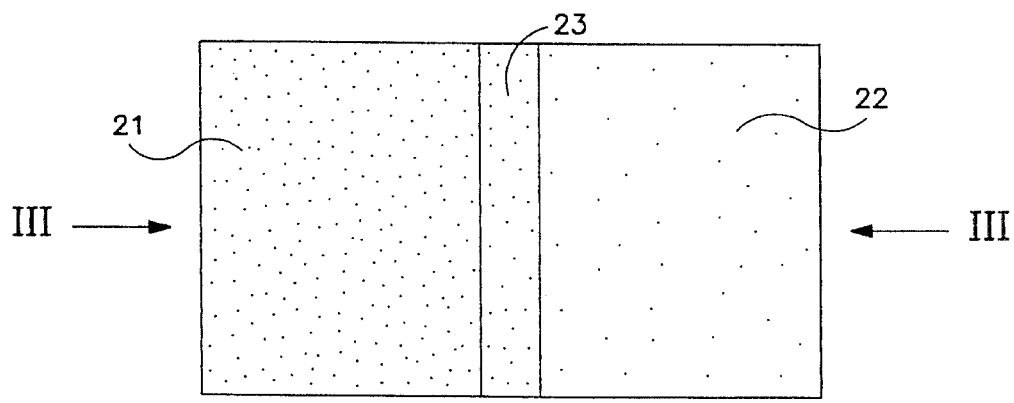
FIG. 2 a plan view of the skin side of a second embodiment of the inventive plaster without a protective layer.

FIG. 2 is a plan view of the skin side of a further inventive angular plaster with a two-part, non-adhesive active substance reservoir, from which the protective layer has already been removed. Thus, on the skin side, the plaster has adhesive layers 21,22, which are separated from one another by the inert reservoir separating layer 23, which can once again be a simple gap or an inert material.

Figure 3:
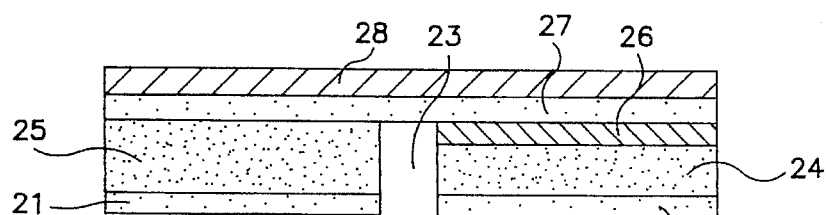
FIG. 3 a cross-section along line III—III of FIG. 2.

FIG. 3 is a cross-section through the embodiment shown in FIG. 2 along line III—III thereof. The non-adhesive active substance reservoir parts 24,25 are fixed at the back by an adhesive layer 27 to the back layer 28, the first active substance reservoir part 24 adhering to the back layer by means of a peel-off layer 26 located between the first adhesive layer 27 and the first active substance reservoir part 24. Peel-off layer 26 is designed in such a way that its adhesion to the first active substance reservoir part 24 is greater than to the adhesive layer 27. Thus, on detaching the back layer 28 and the second active substance reservoir part 25 fixed by means of the adhesive layer 27 to the back layer 28, peel-off layer 26 together with the first active substance reservoir part 24 remains on the skin and assumes for said remaining part 24 the function of a protective layer protecting the reservoir material from contamination and damage from the outside or also against the escape of e.g. volatile active substance components.

The skin side adhesive layers 21,22 on the non-adhesive active substance reservoir parts 24,25 are so adjusted that the adhesion of the adhesive layer 22 of the first active substance reservoir part 24 to the skin is greater than the adhesion between peel-off layer 26 and adhesive layer 27. The differently represented surfaces in the drawing are intended to show that there are different active substances or active substance combinations in both active substance reservoir parts 24,25.

Figure 4:
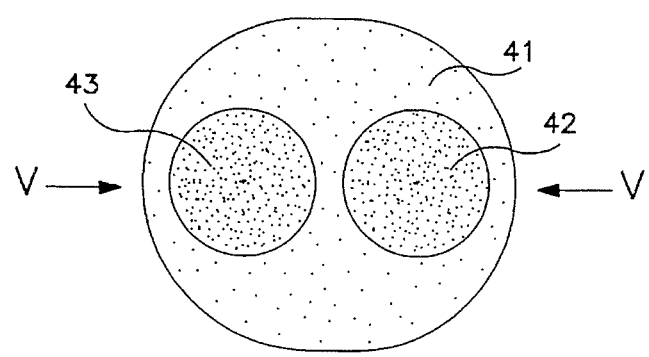
FIG. 4 a plan view of the skin side of a third inventive embodiment without protective layer.

FIG. 4 shows another preferred embodiment of an inventive plaster in plan view on the skin side thereof. The oval plaster has a two-part active substance reservoir and an adhesive layer 41 responsible for the fixing of the active substance reservoir parts 42,43 to the back layer 45 also forms the fastening to the skin of the therapeutic system.

Figure 5:
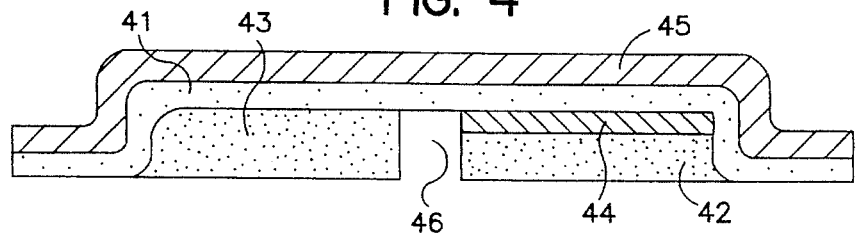
FIG. 5 a cross-section through the embodiment of FIG. 4 along line XI—XI on a larger scale.

FIG. 5 shows a larger scale cross-section along line V—V of FIG. 4. The adhesive active substance reservoir parts 42,43, which are separated from one another by an inert reservoir separating layer 46, in this case in the form of a gap, are surrounded in bag-like manner by the back layer 45 carrying a adhesive layer 41. Here again a separating layer 44 ensures that the adhesion of the first active substance reservoir part 42 to the skin is greater than the adhesion between the peel-off layer 44 and the adhesive layer 41 and also ensures that the first active substance reservoir part 42 left on the skin after detaching the second active substance reservoir part 43 and the back layer 45 is protected by a layer. The two active substance reservoir parts 42,43 contain different active substances or active substance combinations, as is made clear by the arrangement of the surfaces.

Figure 6:
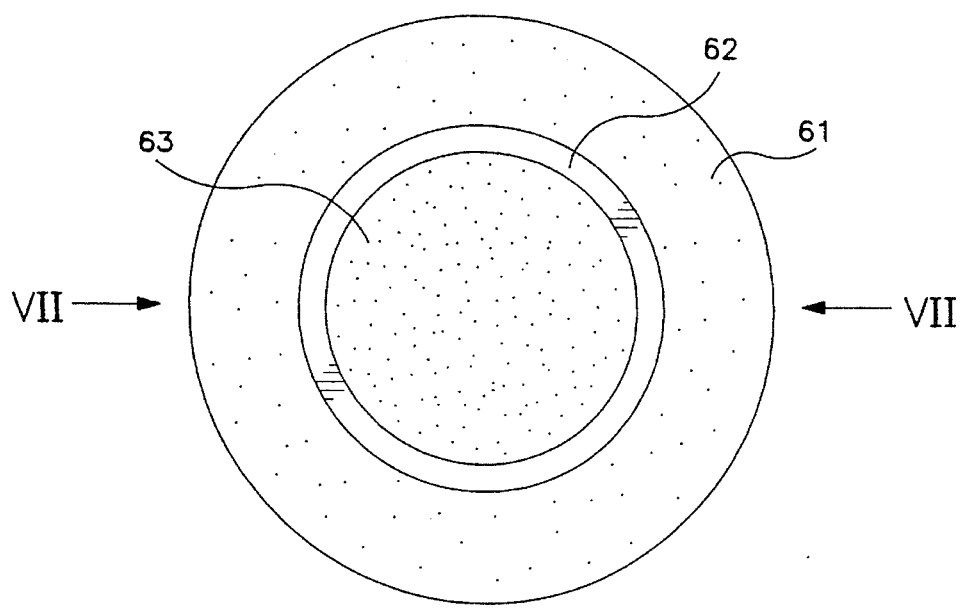
FIG. 6 a plan view of the skin side of a fourth embodiment of the invention without a protective layer.

FIG. 6 shows another inventive plaster with a two-part active substance reservoir, in which one active substance reservoir part 61 concentrically surrounds the other active substance reservoir part 63, the representation being from the skin side and with the protective layer removed. The adhesive, first circular active substance reservoir 63 is separated from the circular second active substance reservoir 61 by an inert reservoir separating layer 62, which can also be in the form of a gap. This embodiment has the advantage that on reducing the active substance release surface by removing part of the plaster with the second active substance reservoir part 61 and together with the back layer 65, it is possible to freely choose the plaster removal direction.

Figure 7:
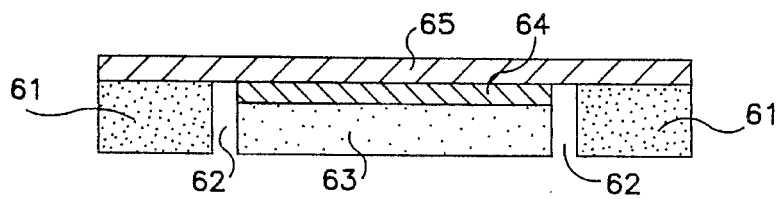
FIG. 7 a cross-section through the embodiment of FIG. 6 along line VII—VII.

FIG. 7 shows a cross-section through the embodiment of FIG. 6 represented along line VII—VII thereof. The circular, second active substance reservoir part 61 is directly adjacent to the back layer 65, while the peel-off layer 64 is arranged between the circular, first active substance reservoir part 63 and the back layer 65. The adhesion of the first active substance reservoir part 63 to the skin and that between the peel-off layer 64 and the back layer 65 is greater than the adhesion between the peel-off layer 64 and active substance reservoir part 63, so that on removing the back layer 65 the second active substance reservoir part 61 is removed, while leaving the first active substance reservoir part 63 on the skin and which is now covered by the peel-off layer 64. The inert reservoir separating layer 62 separates active substance reservoir parts 61,63. In this embodiment, the active substance is the same in both active substance reservoir parts 61,63.

Figure 8:
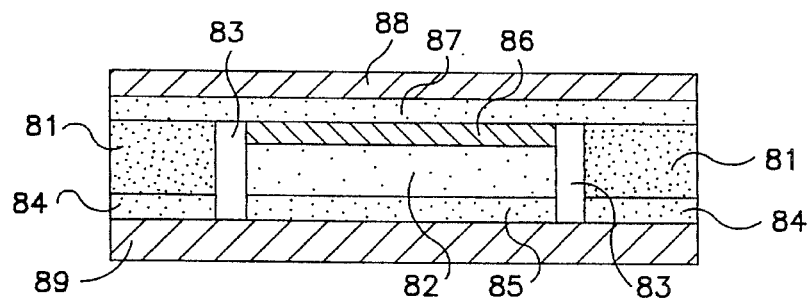
FIG. 8 a cross-section through a fifth embodiment of the invention.

FIG. 8 shows another preferred embodiment of the invention in cross-section, in which the two parts of a non-adhesive active substance reservoir are once again constructed as a circular disk 82 with a surrounding ring 81. They are separated from one another by an inert reservoir separating layer 83. Back layer 88 is covered by an adhesive layer 87, which is directly in contact with the second active substance reservoir part 81.

Between the adhesive layer 87 and the first active substance reservoir part 82 is provided an inert peel-off layer 86, which is so designed that its adhesion to the adhesive layer 87 is less than the adhesion between the adhesive layer 85 and the skin. The remaining adhesion values on the boundary layers of said plaster part must naturally be above the adhesion value to the skin. The skin side adhesive layers 84,85 of the active substance reservoir parts 81,82 ensure contact with the skin and prior to the application of the inventive plaster are advantageously covered by a protective layer 89.

In this embodiment, both active substance reservoir parts 81,82 have different active substances or active substance combinations.

Figure 9:
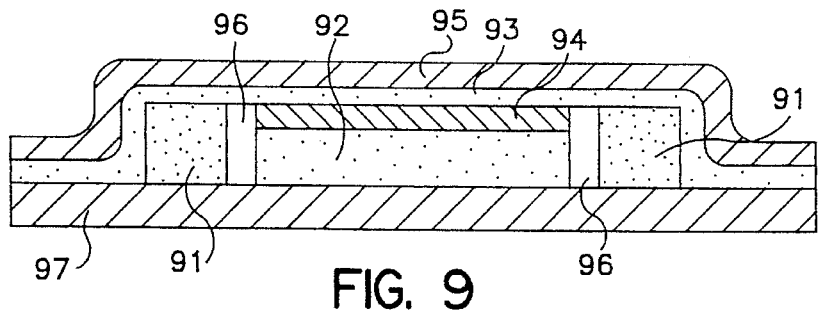
FIG. 9 a cross-section through a sixth embodiment of the invention.

FIG. 9 shows a cross-section through another embodiment of the invention, in which the back layer 95 surrounds the concentric arrangement of the adhesive active substance reservoir parts 91,92 to the skin side. For fixing the overall plaster and the active substance reservoir parts to the skin, the whole surface of back layer 95 is covered with an adhesive layer 93. To the latter adheres the second active substance reservoir part 91 in a direct manner, while the first active substance reservoir part 92 is fixed via a peel-off layer 94. The adhesion of peel-off layer 94 to the active substance reservoir part 92 is above and the adhesion of layer 94 to adhesive layer 93 is below the adhesion between the first active substance reservoir part 92 and the skin. This permits a selective removal of back layer 95 together with the second active substance reservoir part 91. Through a corresponding change to the structure, it is also possible to bring about a selective removal of the first active substance reservoir part 92. Reference numeral 96 designates the inert reservoir separating layer or the gap between the active substance reservoir parts 91,92. Up to application, the overall arrangement is covered by a detachable protective layer 97. The active substances or active substance combinations are different in both reservoir parts 91,92 in this embodiment.

Figure 10:
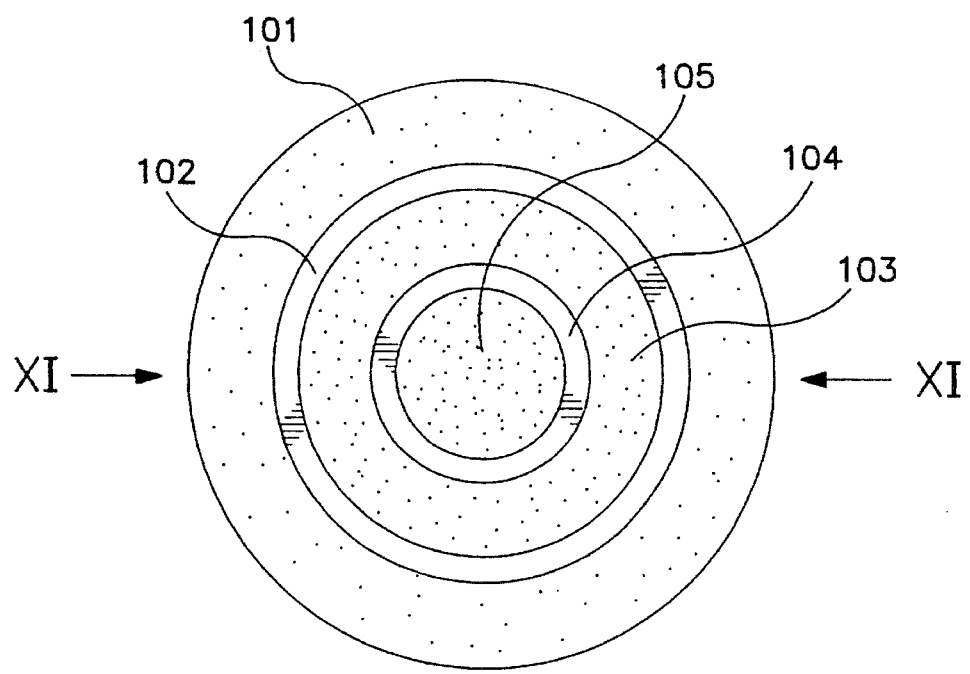
FIG. 10 a plan view of the skin side of another embodiment of an inventive plaster with a three-part active substance reservoir and without a protective layer.

Another preferred embodiment of the invention with a three-part active substance reservoir is shown in FIG. 10. The latter is a plan view of the skin side of an inventive plaster without the protective layer. A first, circular, adhesive active substance reservoir part 105 is surrounded by a second, circular, adhesive active substance reservoir part 103 and is separated therefrom by an inert reservoir separating layer 104. The third adhesive active substance reservoir part 101 surrounds the second active substance reservoir part 103 in concentric ring form. Between the second and third active substance reservoir parts 101,103 is provided a further inert reservoir separating layer 102.

Figure 11:
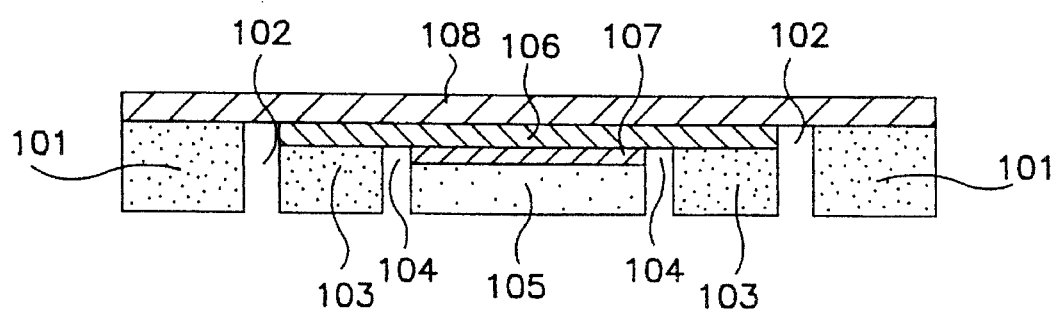
FIG. 11 a larger scale cross-section along line XI—XI of FIG. 10.

FIG. 11 is a larger scale cross-section along line XI—XI. Active substance reservoir part 101 adheres directly to back layer 108. A first peel-off layer 106 connected to back layer 108 covers the active substance reservoir parts 103,105. The adhesion thereof to the back layer 108 is less than the adhesion of the active substance reservoir parts 103,105 to the skin, so that active substance reservoir parts 103,105 remain on the skin on removing the back layer 108 with active substance reservoir part 101. Thus, the first peel-off layer 106 then forms a protective, new layer for the remaining parts of the plaster. The adhesive active substance reservoir part 103 adheres directly to the first peel-off layer 106 and can be removed together with the latter in a further removal step, while leaving behind on the skin the first active substance reservoir part 105 this being made possible by the second peel-off layer 107 between the first active substance reservoir part 105 and the first peel-off layer 106. The adhesion of the second peel-off layer 107 to the first layer 106 is less than the adhesion of the first active substance reservoir part 105 to the skin. The inert reservoir separating layers 102,104, which can also be formed by gaps, are located between active substance reservoir parts 101,103 or 103,105. The chosen example shows for active substance reservoir parts 103,105 the same active substance or active substance combination, indicated by the identical dotting in FIG. 11, while the active substance reservoir part 101 has a different active substance or active substance combination.

The drawings which merely illustrate the invention in an exemplified manner, are not intended to restrict the invention either as regards geometrical shape, the association of specific individual components, or as regards the size of the active substance release surfaces. As is well know to the Expert in this field, all these quantities can be adapted to the therapeutic requirements and obviously account must be taken of rational production. The part of the active substance reservoir part to be detached can also have a peel-off layer, which then has a greater adhesion to the back layer than the peel-off layer of the reservoir part remaining on the skin. This construction is advantageous if the active substance reservoir parts are to have the same thickness. The adhesive layers, particularly those on the skin side, can have non-adhesive areas for improved active substance permeability, or can be constructed solely as individual adhesive surfaces, e.g. can be embedded in the active substance reservoir material. The release of the active substances from the active substance reservoir parts can optionally be regulated by control membranes, which are embedded in per se known manner in the reservoir mass in one or more active substance reservoir parts, or can be located between the active substance reservoir and the skin side adhesive layer, or within the skin side adhesive layer.

For the construction of an active substance reservoir, as used according to the invention, it is possible to use the standard measures and materials. The basic materials can be constituted by low and high molecular weight, natural and/or synthetic substances, whose choice is a function of the characteristics of the active substances to be administered and the therapeutic requirements. Apart from the basic material, the active substance reservoir can also contain further suitable additives known or obvious to the Expert on the basis of his knowledge, such as e.g. solubilizers, softeners, plasticizers, tackifiers, stabilizers, fillers and enhancers. The composition in the reservoir parts can be the same or different, which is once again dependent on the active substances to be administered and the desired release rates or kinetics. In the case of an identical reservoir composition and only one active substance to be administered, it can be appropriate to have a graduated concentration setting of the active substance in the different reservoir parts. Suitable active substances for the inventive plasters are all those which alone or with adjuvants are able to migrate into the skin.

The back layer covering the active substance reservoir on the skin remote side can be permeable or impermeable. It must be flexible and, as a result of the mechanical stabilization of the plaster, serves to remove part of the active substance reservoir. If components of the reservoir or the incorporated active substances are volatile, then the back layer must be impermeable to these substances. It can be in one or multi-layer form. Suitable materials for the production thereof are e.g. polymeric substances, such as polyethylene, polypropylene, polyesters and polyamides. Further materials can be metal foils, such as e.g. aluminum foil, either alone or coated with a polymeric substrate. Permeable back layers are e.g. textile fabrics, such as non-woven fabrics and the like, but also porous polymer materials. The back layer can optionally carry a marking for indicating the optimum plaster removal direction. Optionally peel-off layers are provided between the active substance reservoir parts in place of a gap. They can be constituted by the same materials as described hereinbefore for the separating layer between the active substance reservoir parts and the back layer. The protective layer detachable prior to application and which covers the skin side adhesive surfaces can be made from the same material as used for making the back layer, provided that they can be made detachable, e.g. by applying a silicone layer. Other detachable protective layers, as known to the Expert in the field of plasters and in particular plaster-like therapeutic systems are e.g. polytetrafluoroethylene, treated paper, cellophane, polyvinylchloride, etc. To facilitate detachability, the protective layer can be provided with removal aids in per se known manner. The protective layer can also be larger than the plaster, e.g. if several plasters are arranged on an uninterrupted web of the protective layer material.

Adhesive layers used for the inventive plasters can be constituted by all physiologically unobjectionable adhesives which are inert to active substances and other active substance reservoir components, e.g. can be based on rubber, rubber-like synthetic homoco- or block polymers, polyacrylates and their copolymers, polyurethanes and silicones.

The inventive plaster can be produced by all known plaster technology methods. This is demonstrated in the following production example for a plaster with a two-part active substance reservoir.

Production Example

In a roller application process to a film or foil given a repelling finish by siliconizing and which serves as an intermediate covering, is applied an active substance-containing reservoir material solution and which, after drying at 65° C., forms an adhesive layer of 55 g/m² and having the following composition:

| | | |
|---|---|---|
| 1. | Acrylate copolymer I | 68.86 parts by weight |
| 2. | Acrylate copolymer II | 10.39 parts by weight |
| 3. | POE-(10)-oleyl alcohol | 5.20 parts by weight |
| 4. | Active substance | 15.56 parts by weight |

Acrylate copolymer I is Durotac 280–2516 of National Starch & Chemical B.V., Netherlands; Acrylate copolymer II is Eudragit E100 of Röhm Pharma, Germany; POE-(10)-oleyl alcohol is Brij 97 of Atlas Chemical Industries, GB.

Onto one half of the active substance-containing adhesive layer is applied a non-siliconized polyester film (thickness 0.036 mm) and to the other half the non-siliconized side of a one-sided, siliconized polyester film (thickness 0.036 mm). After removing the intermediate covering ring-like active substance reservoir parts are punched out of the first half and are applied with the adhesive side to a siliconized, aluminum vapor-deposited polyester film (protective layer). From the second half are punched disk-like active substance reservoir parts with a slightly smaller diameter than the internal diameter of the rings into which they are centrally inserted with the adhesive side directed towards the protective layer. The open side of the thus obtained unit is covered by a polyester-based, adhesively finished 0.015 mm thick back layer (Durotac 280–2516, 30 g/m² dry), the outwardly directed side being adhesive-free. The distance between the active substance reservoir units is approximately 14 mm, so that the back layer is in contact with the protective layer between the units. The thus obtained laminate is then supplied to a production process, in which by circular punching at a distance of approximately 7 mm from the outer edge of the rings, all-round closed disk-like plasters are obtained, one or more of which are packed in sealed bags.

We claim:

1. An active substance-containing plaster for the controlled administration of one or more active substances to the skin, comprising a back side and a skin side;

wherein on the back side is a back layer;

wherein on the skin side is an adhesive means and at least two active substance release surfaces;

wherein a first reservoir for a first active substance is in contact with a peel-off layer which is in contact with the back layer on the back side, and forms a first active substance release surface on the skin side;

wherein a second reservoir for a second active substance is in contact with the peel-off layer on the back side, and forms a second active substance release surface on the skin side;

wherein a reservoir separating layer comprising a gap or space between the first and second active substance reservoir or an inert separating material is present between the first and second active substance reservoir to prevent mixing of the first and second active substances;

wherein the second active substance reservoir is detachable by peeling away, the peel-off layer to terminate administration of its active substance through the second active substance release surface;

wherein the first active substance reservoir remains attached to the skin to further administer its active substance; and wherein the first active substance release surface has a better adhesion to the skin than to the peel-off layer.

2. Active substance-containing plaster according to claim 1, characterized in that the first or the second active substance reservoir is in at least two parts.

3. Active substance-containing plaster according to claim 1, characterized in that the active substance release surfaces of the active substance reservoir parts are geometrically identical.

4. Active substance-containing plaster according to claim 1, characterized in that one active substance reservoir part completely surrounds one or more other active substance reservoir parts, considered in a flat or surface manner.

5. Active substance-containing plaster according to claim 1 characterized in that one active substance reservoir part angularly surrounds one or more other active substance reservoir parts.

6. Active substance-containing plaster according to claim 1 characterized in that the release surface-size ratio of one active substance reservoir part to another is between approximately 1:1 and 1:10.

7. A active substance-containing plaster as claimed in claim 1, wherein the active substance is a vasodilator.

8. Active substance-containing plaster according to claim 1 characterized in that at least one active substance reservoir part there is a different active substance/active substance combination as compared with the other active substance reservoir part.

9. Active substance-containing plaster according to claim 1, characterized in that the active substances have a topical action.

10. Process for the controlled administration of one or more active substances to the skin by means of a plaster according to claim 1, characterized by the adhesion to the skin of a plaster having one or more active substances at one or more concentrations in different active substance reservoir parts which can be separated from one another and removal of one or more plaster parts within each case one or more active substance reservoir parts after a predetermined time and while leaving behind a plaster residue with at least one active substance reservoir part on the skin.

11. Process for use of the active substance-containing plaster according to claim 1 characterized by applying the active substance-containing plaster for local and systemic, transdermal active substance administration in human or animal medicine, or in cosmetics.

12. Active substance-containing plaster according to claim 1 which is provided with a cover layer over the adhesive means and the active substance release surface detachable prior to the application of the plaster.

13. A process according to claim 10, wherein the plaster residue left behind has still two active substance reservoir parts on the skin and one of them is separated from the other and removed after a predetermined period of time.

14. Active substance-containing plaster according to claim 1, wherein the active substance release surfaces of the active substance reservoir parts are geometrically different.

15. Active substance-containing plaster according to claim 1, wherein the active substance has a systemic action.

16. Active substance-containing plaster according to claim 1 which is provided with a detachable protective layer over the active substance release surface detachable prior to the application of the plaster.

17. An active substance-containing plaster for the controlled administration of one or more active substances to the skin, comprising a back side and a skin side;

wherein on the back side is a back layer;

wherein on the skin side is an adhesive means and at least two active substance release surfaces;

wherein a first active substance reservoir is in contact with a peel-off layer which is in contact with an adhesive layer which is between the peel-off layer and the back layer on the back side, and forms a first active substance release surface on the skin side;

wherein a second active substance reservoir is in contact with the peel-off layer on the back side, and forms a second active substance release surface on the skin side;

wherein a reservoir separating layer comprising a gap or space between the first and second active substance reservoir or an inert separating material is present between the first and second active substance reservoir to prevent mixing of the first and second active substances;

wherein the second active substance reservoir is detachable by peeling away, the peel-off layer to terminate administration of its active substance through the second active substance release surface;

wherein the first active substance reservoir remains attached to the skin to further administer its active substance; and wherein the first active substance release surface has a better adhesion to the skin than to the peel-off layer.

18. An active substance-containing plaster as claimed in claim 1, wherein the active substance is a bronchodilator.

19. A plaster as claimed in claim 18, wherein the active substance is salbutamol.

20. Active substance-containing plaster according to claim 17 in that the same active substance or same active substance combination is present in all the active substance reservoir parts.

21. An active substance-containing plaster as claimed in claim 1, wherein the active substance is a compound to cause people to stop smoking.

22. A plaster as claimed in claim 17, wherein the active substance is a compound to cause people to stop smoking.

23. A plaster as claimed in claim 21, wherein the compound to cause people to stop smoking is nicotine.

24. A plaster as claimed in claim 21, wherein the compound to cause people to stop smoking is lobeline.

25. A plaster as claimed in claim 17, wherein the first and second active substances are estrogen and gestagen.

26. A plaster as claimed in claim 17, wherein the first and second active substance are dexamethasone and prednisolone.

27. A plaster as claimed in claim 17, wherein the first and second active substance are nitroglycerine and a β-blocker.

28. A plaster as claimed in claim 17, wherein the first and second active substance are amitriptyline and chlordiazepoxide.

29. A plaster as claimed in claim 17, wherein the plaster contains a third reservoir for a third active substance.

30. A plaster as claimed in claim 29 wherein the active substances are phenytoin, phenobarbital and caffeine.

* * * * *